(12) United States Patent
Watabe et al.

(10) Patent No.: US 11,199,493 B2
(45) Date of Patent: Dec. 14, 2021

(54) FUNCTIONAL WATER CONCENTRATION SENSOR, AND CALCULATION METHOD

(71) Applicant: PANASONIC INTELLECTUAL PROPERTY MANAGEMENT CO., LTD., Osaka (JP)

(72) Inventors: Yoshifumi Watabe, Osaka (JP); Ryo Arakawa, Osaka (JP); Toru Baba, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 14 days.

(21) Appl. No.: 16/642,355

(22) PCT Filed: Jul. 20, 2018

(86) PCT No.: PCT/JP2018/027220
§ 371 (c)(1),
(2) Date: Feb. 26, 2020

(87) PCT Pub. No.: WO2019/044249
PCT Pub. Date: Mar. 7, 2019

(65) Prior Publication Data
US 2020/0309682 A1 Oct. 1, 2020

(30) Foreign Application Priority Data

Aug. 28, 2017 (JP) .............................. JP2017-163540

(51) Int. Cl.
*G01N 21/33* (2006.01)
*C25B 1/22* (2006.01)
(Continued)

(52) U.S. Cl.
CPC ............... *G01N 21/33* (2013.01); *C25B 1/22* (2013.01); *G01N 21/645* (2013.01); *G01N 33/18* (2013.01); *G01N 2021/6482* (2013.01)

(58) Field of Classification Search
CPC ...... G01N 21/33; G01N 21/645; G01N 33/18; G01N 2021/6482; G01N 33/182; C25B 1/22
See application file for complete search history.

(56) References Cited

U.S. PATENT DOCUMENTS

| | | | |
|---|---|---|---|
| 4,176,031 A | 11/1979 | Rosenblum | |
| 6,093,292 A * | 7/2000 | Akiyama | ............... C02F 1/4618 204/263 |

(Continued)

FOREIGN PATENT DOCUMENTS

| | | |
|---|---|---|
| JP | S55-139817 A | 11/1980 |
| JP | 59-042693 Y | 12/1984 |

(Continued)

OTHER PUBLICATIONS

Frazer Anne Cornish, et al., "Sporicidal Efficacy of PH-Adjusted Bleach for Control of Bioburden on Production Facility Surfaces," Journal of Industrial Microbiology and Biotechnology, Basingstoke, GB, vol. 40, No. 6, Mar. 27, 2013 (Mar. 27, 2013), pp. 601-611, XP035330700, ISSN: 1367-5435, DOI: 10.1007/S10295-013-1257-7.

(Continued)

Primary Examiner — Marcus H Taningco
(74) Attorney, Agent, or Firm — McDermott Will and Emery LLP (57) ABSTRACT

A functional water concentration sensor includes: a light source which emits ultraviolet light; a container capable of holding functional water having a pH between 6 and 9, inclusive, and containing hypochlorous acid and hypochlorite dissociated from the hypochlorous acid; a light-receiv- (Continued)

ing element; and a signal processor. The signal processor calculates the concentration of the hypochlorite in the functional water on the basis of the output signal, calculates the percentages of the hypochlorous acid and the hypochlorite in the functional water on the basis of the pH of the functional water and the dissociation constant of the hypochlorous acid, and calculates the concentration of the hypochlorous acid in the functional water on the basis of the calculated hypochlorite concentration and the calculated percentages.

12 Claims, 4 Drawing Sheets

(51) Int. Cl.
  *G01N 21/64* (2006.01)
  *G01N 33/18* (2006.01)

(56) References Cited

U.S. PATENT DOCUMENTS

| | | | | |
|---|---|---|---|---|
| 10,746,653 | B2* | 8/2020 | Kraus | G01N 21/33 |
| 2015/0068914 | A1* | 3/2015 | Brondum | C25B 1/265 |
| | | | | 205/335 |
| 2015/0343386 | A1* | 12/2015 | Labib | C11D 3/3956 |
| | | | | 210/636 |
| 2017/0248568 | A1* | 8/2017 | Yizhack | G01J 3/42 |
| 2018/0284014 | A1 | 10/2018 | Suehiro et al. | |
| 2020/0182828 | A1* | 6/2020 | Einaga | G01N 27/49 |

FOREIGN PATENT DOCUMENTS

| | | | |
|---|---|---|---|
| JP | S61-33605 | B2 | 8/1986 |
| JP | H09-155358 | A | 6/1997 |
| JP | 2000-343080 | A | 12/2000 |
| JP | 2001-124732 | A | 5/2001 |
| JP | 2001-194307 | A | 7/2001 |
| JP | 2003-130792 | A | 5/2003 |
| JP | 2003-240712 | A | 8/2003 |
| JP | 2003240712 | A * | 8/2003 |
| JP | 2014-190660 | A | 10/2014 |
| JP | 2016-136122 | A | 7/2016 |
| JP | 2017-032503 | A | 2/2017 |
| JP | 2017-064621 | A | 4/2017 |
| JP | 2017-120246 | A | 7/2017 |
| WO | 2017/010043 | A1 | 1/2017 |

OTHER PUBLICATIONS

Extended European Search Report dated Oct. 5, 2020, issued in European Patent Application No. 18851121.6.

International Search Report and Written Opinion dated Oct. 16, 2018 in International Application No. PCT/JP2018/027220; with partial English translation.

* cited by examiner

FUNCTIONAL WATER CONCENTRATION SENSOR, AND CALCULATION METHOD

CROSS-REFERENCE OF RELATED APPLICATIONS

This application is the U.S. National Phase under 35 U.S.C. § 371 of International Patent Application No. PCT/JP2018/027220, filed on Jul. 20, 2018, which in turn claims the benefit of Japanese Application No. 2017-163540, filed on Aug. 28, 2017, the entire disclosures of which Applications are incorporated by reference herein.

TECHNICAL FIELD

The present invention relates to functional water concentration sensors and calculation methods.

BACKGROUND ART

Absorptiometry is known as a method for measuring the concentration of functional water such as hypochlorous acid water and ozonated water. Patent Literature (PTL) 1 discloses a chloride concentration monitoring device which uses the absorptiometry.

CITATION LIST

Patent Literature

PTL 1: Japanese Unexamined Patent Application Publication No. 2003-130792

SUMMARY OF THE INVENTION

Technical Problem

In the aforementioned chloride concentration monitoring device, in order to calculate an effective chloride concentration value of electrolytic hypochlorite water, the process for correcting, at a dilution ratio, the absorbance of an aqueous mixture obtained by mixing the electrolytic hypochlorite water with strong alkaline water is performed. In other words, the process for calculating the effective chloride concentration value is complex.

The present invention provides a functional water concentration sensor and a calculation method which enable the concentration of hypochlorous acid in functional water to be easily calculated.

Solution to Problem

A functional water concentration sensor according to one aspect of the present invention includes: a light source which emits ultraviolet light; a container including an entry window through which the ultraviolet light enters and an exit window through which the ultraviolet light that has entered the container through the entry window exits, the container being capable of holding functional water having a pH between 6 and 9, inclusive, and containing hypochlorous acid and hypochlorite dissociated from the hypochlorous acid; a light-receiving element which includes a light-receiving surface facing the exit window and outputs an output signal according to an amount of light incident on the light-receiving surface; and a signal processor. The signal processor calculates a concentration of the hypochlorite in the functional water based on the output signal, calculates percentages of the hypochlorous acid and the hypochlorite in the functional water based on the pH of the functional water and a dissociation constant of the hypochlorous acid, and calculates a concentration of the hypochlorous acid in the functional water based on the concentration of the hypochlorite calculated and the percentages calculated.

A calculation method according to one aspect of the present invention is a method for calculating a concentration of hypochlorous acid in functional water using a functional water concentration sensor including: a light source which emits ultraviolet light; a container including an entry window through which the ultraviolet light enters and an exit window through which the ultraviolet light that has entered the container through the entry window exits, the container being capable of holding the functional water having a pH between 6 and 9, inclusive, and containing the hypochlorous acid and hypochlorite dissociated from the hypochlorous acid; and a light-receiving element which includes a light-receiving surface facing the exit window and outputs an output signal according to an amount of light incident on the light-receiving surface. The calculation method includes: calculating a concentration of the hypochlorite in the functional water based on the output signal; calculating percentages of the hypochlorous acid and the hypochlorite in the functional water based on the pH of the functional water and a dissociation constant of the hypochlorous acid; and calculating a concentration of the hypochlorous acid in the functional water based on the concentration of the hypochlorite calculated and the percentages calculated.

Advantageous Effect of Invention

The present invention makes it possible to provide a functional water concentration sensor and a calculation method which enable the concentration of hypochlorous acid in functional water to be easily calculated.

DESCRIPTION OF EXEMPLARY EMBODIMENTS

Hereinafter, exemplary embodiments will be described in detail with reference to the drawings. Note that each of the exemplary embodiments described below shows a specific preferred example of the present invention. Thus, the numerical values, shapes, materials, structural elements, and the arrangement and connection of the structural elements, etc., shown in the following exemplary embodiments are mere examples, and are not intended to limit the present invention. Accordingly, among the structural elements in the following exemplary embodiments, structural elements not recited in an independent claim indicating the broadest concept of the present invention are described as arbitrary structural elements.

The figures are schematic diagrams and are not necessarily precise illustrations. Additionally, like structural elements share like reference numerals in the figures. In the following exemplary embodiments, the terms such as "substantially the whole" and "substantially the same" are used. For example, in addition to meaning exactly the same, "substantially the same" means essentially the same, i.e., includes deviations of about a few percent. This applies to other terms where "substantially" is used as well.

Embodiment 1

Outline of Functional Water Concentration Sensor

Figure 1:
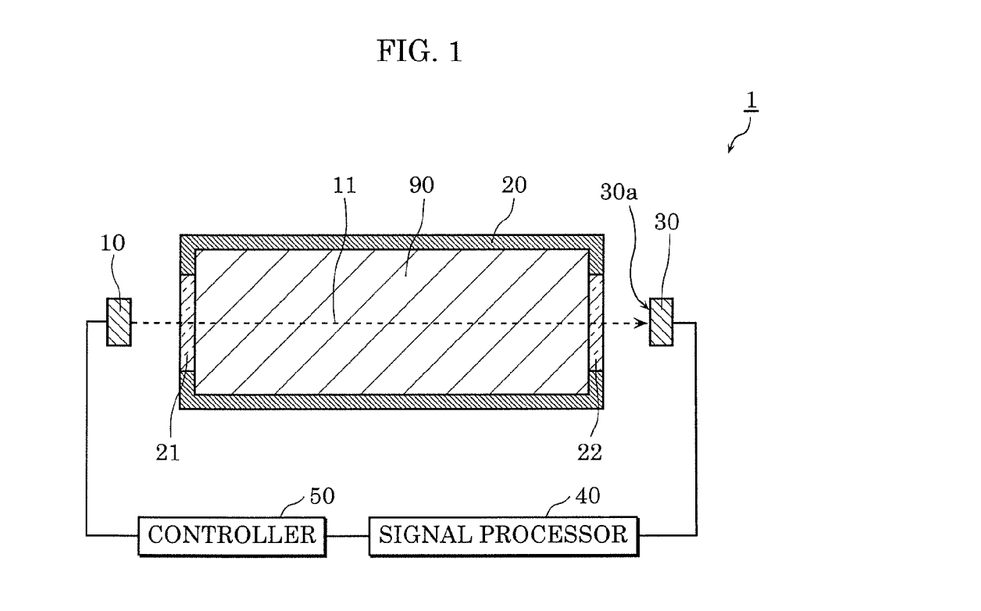
FIG. 1 is a schematic diagram illustrating the configuration of a functional water concentration sensor according to Embodiment 1.

First, the outline of a functional water concentration sensor according to Embodiment 1 will be described with reference to FIG. 1. FIG. 1 is a schematic diagram illustrating the configuration of a functional water concentration sensor according to Embodiment 1.

Functional water concentration sensor 1 according to Embodiment 1 measures the concentration of functional water 90 contained in container 20. Specifically, functional water concentration sensor 1 emits ultraviolet light 11 to functional water 90, detects, by light-receiving element 30, ultraviolet light 11 that has passed through functional water 90, and thus measures the concentration of functional water 90.

Functional water 90 is an aqueous solution which, among those provided with useful functions reproducible by artificial processes, has the scientific basis for such process and function already established or to be established.

In Embodiment 1, functional water 90 is hypochlorous acid water and contains hypochlorous acid and hypochlorite dissociated from the hypochlorous acid. Furthermore, functional water 90 contains a pH adjuster and is controlled to have a constant pH value. The pH of functional water 90 is controlled to have a constant value between 6 and 9, inclusive, for example. This leads to a reduction in the occurrence of both of the hypochlorous acid concentration and the hypochlorite concentration being extremely high or low. Functional water concentration sensor 1 is used, for example, in a space cleaner that performs air disinfection and deodorization using hypochlorous acid.

As illustrated in FIG. 1, functional water concentration sensor 1 includes light source 10, container 20, light-receiving element 30, signal processor 40, and controller 50. Note that although not illustrated in FIG. 1, functional water concentration sensor 1 is housed in a light-blocking casing in order to keep external light from entering light-receiving element 30. In the case where this casing is formed of a material that absorbs ultraviolet light 11, light that has not entered entry window 21 (namely, stray light) out of ultraviolet light 11 emitted by light source 10 can be absorbed by the casing.

Hereinafter, structural elements included in functional water concentration sensor 1 will be described in detail.

Light Source

Light source 10 emits ultraviolet light 11. Ultraviolet light 11 has a peak wavelength of 350 nm or less, for example. Details of ultraviolet light 11 will be described later.

Light source 10 may be capable of changing the peak wavelength of ultraviolet light 11. Specifically, light source 10 may emit ultraviolet light 11 having a peak wavelength different depending on functional water 90 which is a measurement target. In other words, light source 10 may emit, as ultraviolet light 11, light having a peak wavelength predetermined on the basis of an absorption spectrum unique to functional water 90. In the case where functional water 90 is hypochlorous acid water, light source 10 emits ultraviolet light 11 having a peak wavelength in the range of 250 nm to 350 nm, inclusive.

Light source 10 is, for example, a solid-state light-emitting element such as a light-emitting diode (LED), but is not limited to the solid-state light-emitting element. Light source 10 may be a semiconductor laser, a compact mercury lamp, or the like.

Light source 10 is disposed facing entry window 21 of container 20. For example, light source 10 is disposed near entry window 21. The term "near" means that the distance between the elements is within a predetermined range and includes the case where the elements are in contact with each other.

This allows substantially the whole of ultraviolet light 11 emitted by light source 10 to enter entry window 21. In other words, ultraviolet light 11 emitted by light source 10 is kept from leaking outside container 20. Ultraviolet light 11 from light source 10 substantially perpendicularly enters entry window 21.

Container

Container 20 can hold functional water 90. Container 20 is, for example, a bottomed cylindrical cell such as a bottomed circular cylinder or a bottomed rectangular cylinder, but is not limited to the bottomed cylindrical cell. Container 20 includes two transmissive windows through which ultraviolet light 11 passes. Specifically, container 20 includes entry window 21 and exit window 22.

Entry window 21 is a window through which ultraviolet light 11 emitted from light source 10 enters. Entry window 21 is formed of a light-transmissive member that is provided in an opening of container 20 and allows passage of ultraviolet light 11. For example, entry window 21 is formed of quartz glass, sapphire glass, or the like. Entry window 21 is in the shape of a plate having substantially flat entry and exit surfaces. Ultraviolet light 11 substantially perpendicularly enters entry window 21. Specifically, ultraviolet light 11 is incident along the thickness of entry window 21. In other words, ultraviolet light 11 is incident in the normal direction to the entry surface.

Exit window 22 is a window through which ultraviolet light 11 that has entered container 20 exits. Exit window 22 is formed of a light-transmissive member that is provided in an opening of container 20 and allows passage of ultraviolet light 11. For example, exit window 22 is formed of quartz glass, sapphire glass, or the like. Specifically, exit window 22 is in the shape of a plate having substantially flat entry and exit surfaces. Ultraviolet light 11 is substantially perpendicularly emitted through exit window 22. Specifically, ultraviolet light 11 is emitted along the thickness of exit window 22. In other words, ultraviolet light 11 is emitted in the normal direction to the exit surface.

In Embodiment 1, the main body (specifically, parts other than the two transmissive windows) of container 20 is formed of a material that shields (absorbs or reflects) ultraviolet light 11. For example, the main body of container 20 is formed of a resin material such as acrylic (poly(methyl methacrylate) (PMMA)) and polycarbonate (PC) or a metal material. Note that as a whole, container 20 may be transmissive to ultraviolet light 11. Specifically, the whole of container 20 may be formed of quartz glass or the like.

Note that container 20 may be a portion of predetermined piping. Specifically, functional water 90 may flow in container 20. For example, functional water 90 may circulate between container 20 and a reactor (not illustrated in the drawings). The reactor is a container for allowing functional water 90 to exhibit functions. For example, in the case where functional water 90 has functions such as disinfection and deodorization, functional water 90 comes into contact with an object (for example, a gas such as air) in the reactor to disinfect and deodorize the object. In this case, functional water concentration sensor 1 can measure the concentration of functional water 90 while functional water 90 performs disinfection, deodorization, etc. This means that functional water concentration sensor 1 can be built into deodorization equipment or the like and used.

Light-Receiving Element

Light-receiving element 30 includes light-receiving surface 30a facing exit window 22 and receives, by light-receiving surface 30a, ultraviolet light 11 that is emitted through exit window 22. Specifically, light-receiving element 30 performs photoelectric conversion on received ultraviolet light 11 and thus generates an output signal according to an amount of light incident on light-receiving surface 30a. The generated output signal is output to signal processor 40.

Light-receiving element 30 is a photodiode that is highly sensitive to the ultraviolet region of 380 nm or less, but is not limited to the photodiode. Light-receiving element 30 may be a phototransistor or the like.

Light-receiving element 30 is disposed near exit window 22. This makes it possible to receive substantially the whole light traveling toward light-receiving element 30.

In Embodiment 1, light source 10, container 20, and light-receiving element 30 are arranged in this order on substantially the same straight line. As illustrated in FIG. 1, entry window 21 and exit window 22 of container 20 are also arranged on said straight line. This allows ultraviolet light 11 emitted from light source 10 to travel the shortest distance to light-receiving element 30. Thus, it is possible to reduce generation of stray light between light source 10 and light-receiving element 30.

Note that a phosphor plate containing phosphor that diffuses ultraviolet light 11 and converts the wavelength thereof may be disposed between exit window 22 and light-receiving element 30. If ultraviolet light 11 is converted into visible light in the wavelength conversion through the phosphor plate, a generous-purpose, low-cost element that is almost insensitive to the ultraviolet region can be used as light-receiving element 30.

Signal Processor

Signal processor 40 performs signal processing using the output signal from light-receiving element 30 and calculates the concentration of hypochlorous acid in functional water 90. Signal processor 40 includes, for example, a nonvolatile memory having a program stored therein, a volatile memory which is a temporary storage region for executing the program, an input/output port, and a processor which executes the program. Signal processor 40 is provided, for example, using a microcontroller or the like. The method for calculating the hypochlorous acid concentration will be described later.

Controller

Controller 50 is a control circuit which controls light source 10. For example, controller 50 controls turning on and off of light source 10. Controller 50 controls the intensity, wavelength, etc., of ultraviolet light 11. Furthermore, controller 50 may perform a feedback control on light source 10 on the basis of the result of measuring the concentration of functional water 90 that is output from signal processor 40. For example, when the amount of received light detected by light-receiving element 30 is too small, in other words, when the concentration of hypochlorite in functional water 90 is too low, the intensity or wavelength of ultraviolet light 11 may be made different.

Method for Calculating Hypochlorous Acid Concentration

Figure 2:
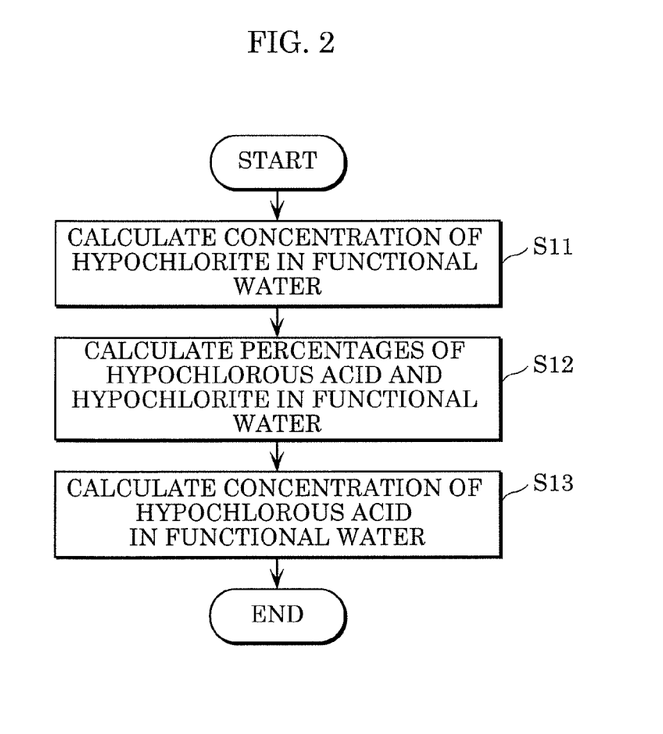
FIG. 2 is a flowchart of a method for measuring the concentration of hypochlorous acid in functional water by a signal processor.

Next, the method for measuring the concentration of hypochlorous acid in functional water 90 by signal processor 40 will be described. FIG. 2 is a flowchart of the method for measuring the concentration of hypochlorous acid in functional water 90 by signal processor 40.

First, on the basis of an electrical signal output from light-receiving element 30, signal processor 40 calculates the concentration of hypochlorite in functional water 90 (S11). Specifically, signal processor 40 calculates the intensity of ultraviolet light 11 on the basis of the electrical signal and calculates the transmittance (or absorbance) of functional water 90 on the basis of the calculated intensity of ultraviolet light 11. Signal processor 40 calculates the concentration of functional water 90 from the calculated transmittance according to the Beer-Lambert law. According to the Beer-Lambert law, the transmittance and the absorbance satisfy Equation 1 and Equation 2 indicated below where $I_0$ represents the intensity of light that has not yet entered a medium and I represents the intensity of light that has passed through a medium having length L.

[Math. 1]

$$\text{Transmittance} = \frac{\text{Intensity } I \text{ of transmitted light}}{\text{Intensity } I_0 \text{ of incident light}} = e^{-aLC} \quad \text{Equation 1}$$

$$\text{Absorbance} = 1 - \text{Transmittance} \quad \text{Equation 2}$$

Here, "a" represents an absorption coefficient, and "C" represents the molar concentration of the medium. And "L" represents the length (that is, the optical path length) of the medium (that is, functional water 90) through which ultraviolet light 11 passes, and in Embodiment 1, corresponds to the distance between entry window 21 and exit window 22 of container 20.

The absorbance indicates the ratio at which functional water 90 absorbs ultraviolet light 11; the larger the value of the absorbance is, the more the absorption by functional water 90 is. For example, an absorbance of "1" indicates that the whole of ultraviolet light 11 is absorbed, and an absorbance of "0" indicates that no ultraviolet light 11 is absorbed at all. Note that the transmittance indicates the transmissivity of functional water 90 to ultraviolet light 11.

In a predetermined range including the absorption peak of functional water 90, the absorbance increases as the concentration of hypochlorite that absorbs ultraviolet light 11 increases, and the absorbance decreases as the concentration of hypochlorite that absorbs ultraviolet light 11 decreases. On the basis of this relationship, signal processor 40 can calculate the concentration of hypochlorite in functional water 90.

Note that signal processor 40 may previously store, into the memory, a table in which the intensity of ultraviolet light 11 and the concentration of hypochlorite in functional water 90 are associated with each other, and calculate the concentration of hypochlorite in functional water 90 with reference to the table.

Next, signal processor 40 calculates the percentages of hypochlorous acid and hypochlorite in functional water 90 on the basis of the pH of functional water 90 and dissociation constant pKa of the hypochlorous acid (S12). Using dissociation constant pKa, the pH of functional water 90 is expressed in Equation 3 indicated below.

[Math. 2]

$$pH = pKa + \log_{10} \frac{[ClO^-]}{[HClO]} \quad \text{Equation 3}$$

Figure 3:
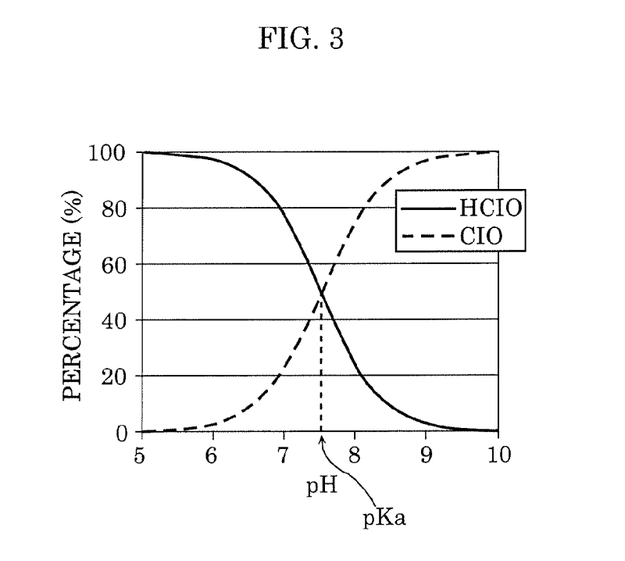
FIG. 3 illustrates the relationship between pH and the percentages of hypochlorous acid and hypochlorite.

Thus, the percentages of hypochlorous acid and hypochlorite can be calculated on the basis of the pH of functional water 90 and dissociation constant pKa of the hypochlorous acid. FIG. 3 illustrates the relationship between the pH and the percentages of hypochlorous acid and hypochlorite. Dissociation constant pKa of the hypochlorous acid is 7.54, and when the pH of functional water 90 is the same as dissociation constant pKa, the percentages of the hypochlorous acid and the hypochlorite is 50% hypochlorous acid and 50% hypochlorite.

As described above, in Embodiment 1, the pH of functional water 90 is controlled by the pH adjuster to have a constant value between 6 and 9, inclusive. For example, when this constant value, dissociation constant pKa, and Equation 3 indicated above are stored in the memory of signal processor 40, signal processor 40 can calculates the percentages of the hypochlorous acid and the hypochlorite.

Next, signal processor 40 calculates the concentration of hypochlorous acid in functional water 90 on the basis of the hypochlorite concentration calculated in Step S11 and the percentages calculated in Step S12 (S13). For example, when the percentages of the hypochlorous acid and the hypochlorite is 40% hypochlorous acid and 60% hypochlorite, the concentration of hypochlorous acid in functional water 90 is the concentration of hypochlorite in functional water 90 multiplied by 40/60.

In this manner, functional water concentration sensor 1 can easily calculate the concentration of hypochlorous acid in functional water 90 on the basis of the pH of functional water 90.

pH Adjuster

The pH adjuster contained in functional water 90 will be described. The pH adjuster is added to functional water 90 in order to control the pH of functional water 90 to have a constant value between 6 and 9, inclusive. The pH adjuster is, for example, an aqueous solution containing at least two types of salt. For example, the absorbance of ultraviolet light 11 by the pH adjuster is less than the absorbance of ultraviolet light 11 by the hypochlorite. Thus, upon calculation of the hypochlorite concentration in Step S11 described above, the effects of absorption of ultraviolet light 11 by the pH adjuster are small, making it possible to improve the accuracy in calculating the hypochlorite concentration.

Furthermore, the pH adjuster has low reactivity with each of the hypochlorous acid and the hypochlorite, for example. This leads to reductions in variations in the hypochlorous acid concentration and variations in the hypochlorite concentration that result from the pH adjuster being contained, making it possible to improve the accuracy in calculating the hypochlorous acid concentration. As the pH adjuster, an agent that has no reactivity with each of the hypochlorous acid and the hypochlorite may be used.

An example of the pH adjuster that has low absorbance of ultraviolet light 11 and has low reactivity with each of the hypochlorous acid and the hypochlorite as just described is a phosphate buffer. Note that the pH adjuster is not limited to the phosphate buffer; it is sufficient that an appropriate agent be selected and used as the pH adjuster.

When the pH of functional water 90 is extremely high, for example, beyond 10, the percentage of the hypochlorite contained in functional water 90 is high, meaning that the relative accuracy of the hypochlorite concentration is high. However, since the percentage of the hypochlorous acid contained in functional water 90 is low, the relative accuracy of the hypochlorous acid concentration calculated on the basis of the hypochlorite concentration is low. This is also true in the case where the pH of functional water 90 is extremely low. Note that the relative accuracy is expressed as a variation percentage where the concentration is 1; a lower variation percentage means higher accuracy.

Thus, the pH of functional water 90 is controlled to have a constant value between 6 and 9, inclusive. As illustrated in FIG. 3, when the pH of functional water 90 is between 6 and 9, inclusive, both the percentage of the hypochlorous acid and the percentage of the hypochlorite can be kept from becoming extremely low. Accordingly, it is possible to increase the accuracy in calculating the hypochlorous acid concentration.

Furthermore, for example, when the pH of functional water 90 is within the range of plus and minus one from dissociation constant pKa of the hypochlorous acid, each of the percentage of the hypochlorous acid and the percentage of the hypochlorite does not fall below 10%. In other words, each of the percentage of the hypochlorite contained in functional water 90 and the percentage of the hypochlorous acid contained in functional water 90 does not become low, making it possible to increase the accuracy in calculating the hypochlorous acid concentration. Ideally, the pH of functional water 90 is the same as dissociation constant pKa of the hypochlorous acid.

Embodiment 2

Configuration

Figure 4:
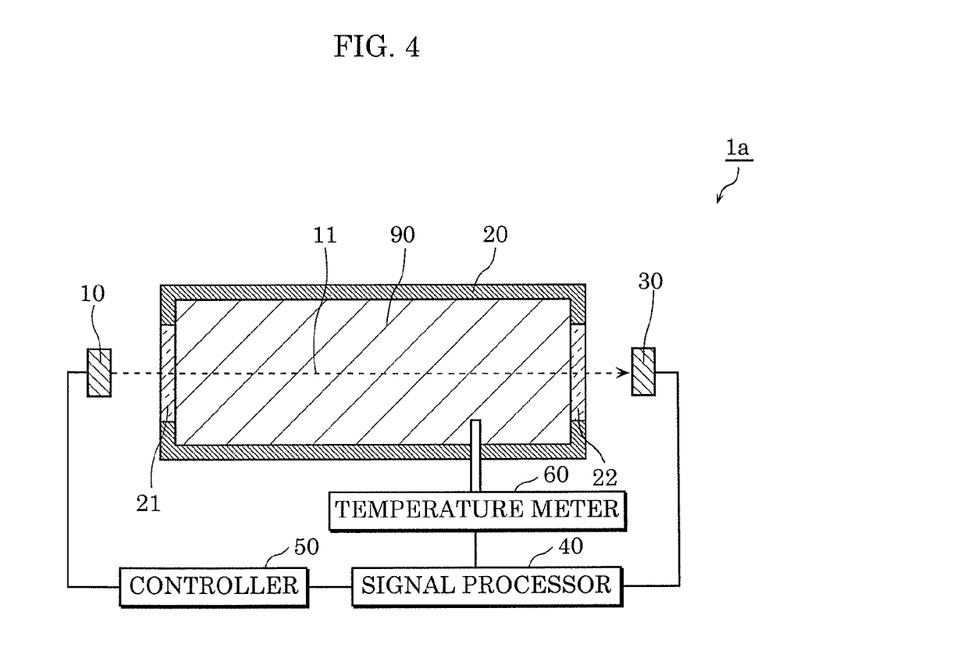
FIG. 4 is a schematic diagram illustrating the configuration of a functional water concentration sensor according to Embodiment 2.

Hereinafter, the configuration of a functional water concentration sensor according to Embodiment 2 will be described with reference to FIG. 4. FIG. 4 is a schematic diagram illustrating the configuration of the functional water concentration sensor according to Embodiment 2. Note that in Embodiment 2 indicated below, differences from Embodiment 1 will be mainly described, and description of matters already mentioned will be omitted, as appropriate.

As illustrated in FIG. 4, functional water concentration sensor 1a includes light source 10, container 20, light-receiving element 30, signal processor 40, controller 50, and temperature meter 60. Functional water concentration sensor 1a is different from functional water concentration sensor 1 in that temperature meter 60 is included.

Temperature meter 60 measures the temperature of functional water 90. Temperature meter 60 is, for example, a sensor including a temperature-measuring element such as a thermocouple or a thermistor. It is sufficient that temperature meter 60 can directly or indirectly measure the temperature of functional water 90; for example, temperature meter 60 may be a non-contact temperature sensor.

OPERATION EXAMPLE 1

Figure 5:
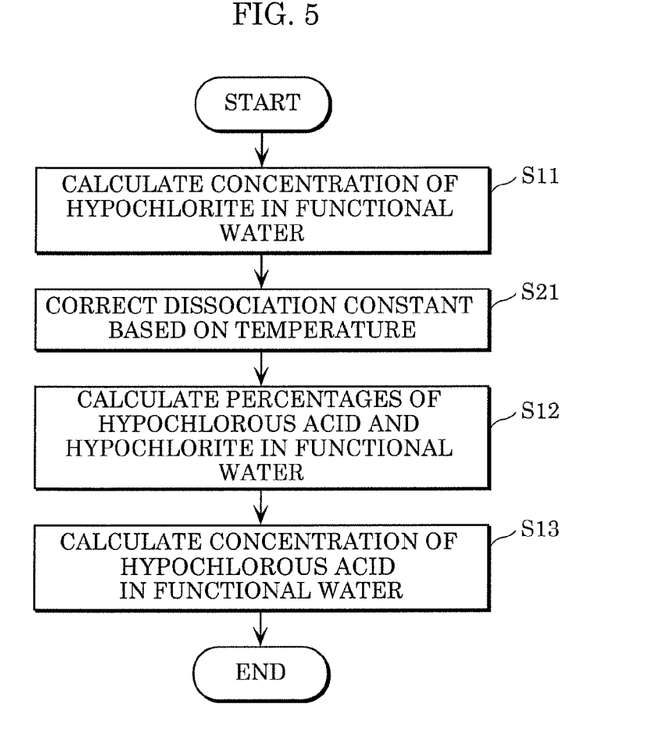
FIG. 5 is a flowchart in Operation Example 1 of a functional water concentration sensor according to Embodiment 2.

Next, Operation Example 1 of functional water concentration sensor 1a will be described. FIG. 5 is a flowchart in Operation Example 1 of functional water concentration sensor 1a.

First, on the basis of the electrical signal output from light-receiving element 30, signal processor 40 calculates the concentration of hypochlorite in functional water 90 (S11).

Figure 6:
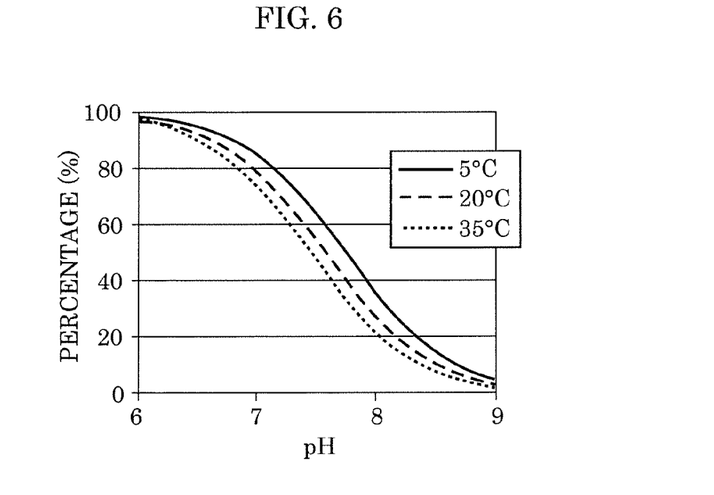
FIG. 6 illustrates changes in temperature in the relationship between pH and the percentages of hypochlorous acid and hypochlorite.

Next, signal processor 40 corrects dissociation constant pKa of the hypochlorous acid on the basis of the temperature of functional water 90 measured by temperature meter 60 (S21). Dissociation constant pKa, which is 7.54 in a 25° C. environment, varies depending on the temperature. Thus, according to Equation 3 indicated above, the relationship between the pH and the percentages of the hypochlorous acid and the hypochlorite also varies depending on the temperature. FIG. 6 illustrates changes in temperature in the relationship between the pH and the percentages of the hypochlorous acid and the hypochlorite.

Thus, in Operation Example 1, signal processor 40 corrects dissociation constant pKa according to the temperature of functional water 90 in Step S21. For example, when dissociation constant pKa in the 25° C. environment, i.e., 7.54, is stored in the memory of signal processor 40, this dissociation constant pKa is corrected according to the temperature.

Subsequently, signal processor 40 calculates the percentages of the hypochlorous acid and the hypochlorite in functional water 90 on the basis of the pH of functional water 90 and corrected dissociation constant pKa of the hypochlorous acid (S12). Furthermore, signal processor 40 calculates the concentration of hypochlorous acid in functional water 90 on the basis of the calculated hypochlorite concentration and the calculated percentages (S13).

By correcting dissociation constant pKa of the hypochlorous acid on the basis of the temperature of functional water 90 in this manner, it is possible to increase the accuracy in calculating the concentration of hypochlorous acid in functional water 90.

OPERATION EXAMPLE 2

Figure 7:
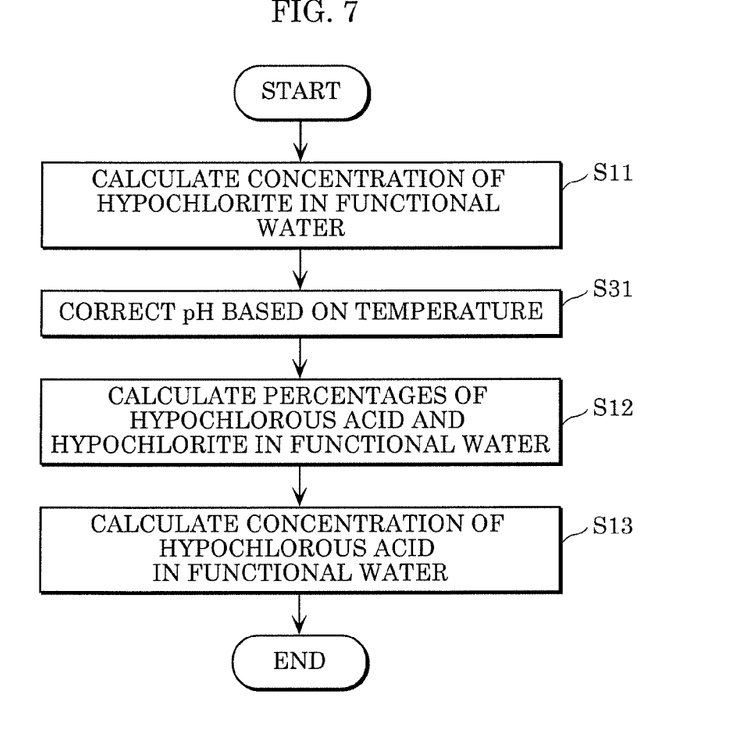
FIG. 7 is a flowchart in Operation Example 2 of a functional water concentration sensor according to Embodiment 2.

Next, Operation Example 2 of functional water concentration sensor 1a will be described. FIG. 7 is a flowchart in Operation Example 2 of functional water concentration sensor 1a.

First, on the basis of the electrical signal output from light-receiving element 30, signal processor 40 calculates the concentration of hypochlorite in functional water 90 (S11).

Next, signal processor 40 corrects the pH of functional water 90 on the basis of the temperature of functional water 90 measured by temperature meter 60 (S31). As described above, the pH of functional water 90 is controlled by the pH adjuster to have a constant value; however, the pH in this case varies according to a change in temperature from a reference temperature (for example, 25° C.).

Thus, in Operation Example 2, signal processor 40 corrects the pH according to the temperature of functional water 90 in Step S31. For example, when the pH of functional water 90 in the 25° C. environment is stored in the memory of signal processor 40, this pH is corrected according to the temperature.

Subsequently, signal processor 40 calculates the percentages of the hypochlorous acid and the hypochlorite in functional water 90 on the basis of the corrected pH of functional water 90 and dissociation constant pKa of the hypochlorous acid (S12). Furthermore, signal processor 40 calculates the concentration of hypochlorous acid in functional water 90 on the basis of the calculated hypochlorite concentration and the calculated percentages (S13).

By correcting the pH of functional water 90 on the basis of the temperature of functional water 90 in this manner, it is possible to increase the accuracy in calculating the concentration of hypochlorous acid in functional water 90.

Modification

Note that Operation Example 1 and Operation Example 2 may be combined. Specifically, signal processor 40 may correct both dissociation constant pKa of the hypochlorous acid and the pH of functional water 90 on the basis of the temperature of functional water 90 and calculate the percentages of the hypochlorous acid and the hypochlorite in functional water 90 on the basis of the corrected pH of functional water 90 and corrected dissociation constant pKa of the hypochlorous acid.

Functional water concentration sensor 1a may include, instead of temperature meter 60, a temperature adjustment device which maintains the temperature of functional water 90 at the reference temperature. With this, signal processor 40 can increase the accuracy in calculating the concentration of hypochlorous acid in functional water 90 without correcting dissociation constant pKa of the hypochlorous acid or the pH of functional water 90.

Embodiment 3

Configuration

Figure 8:
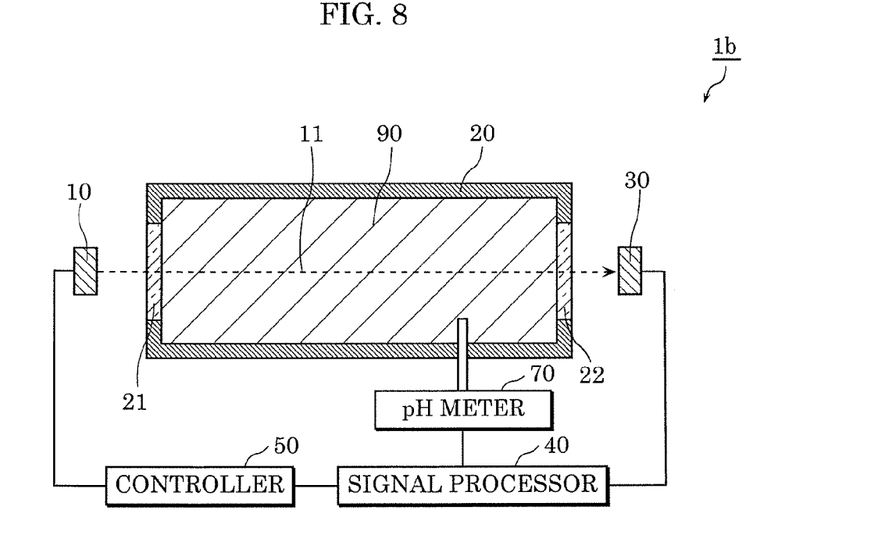
FIG. 8 is a schematic diagram illustrating the configuration of a functional water concentration sensor according to Embodiment 3.

In Embodiments 1 and 2 indicated above, the pH of functional water 90 is controlled by the pH adjuster, but it is not essential that functional water 90 contains the pH adjuster. The method for calculating the hypochlorous acid concentration described in Embodiments 1 and 2 indicated above can be implemented as long as the pH of functional water 90 is obtained. For example, functional water concentration sensor 1 may further include a pH meter which measures the pH of functional water 90. FIG. 8 is a schematic diagram illustrating the configuration of a functional water concentration sensor according to Embodiment 3.

As illustrated in FIG. 8, functional water concentration sensor 1b includes light source 10, container 20, light-receiving element 30, signal processor 40, controller 50, and pH meter 70. Functional water concentration sensor 1b is different from functional water concentration sensor 1 in that pH meter 70 is included.

pH meter 70 measures the pH of functional water 90. pH meter 70 is, for example, a glass-electrode pH meter, and other pH meters may be used.

In functional water concentration sensor 1b, signal processor 40 calculates the percentages of the hypochlorous acid and the hypochlorite in functional water 90 on the basis of the measured pH of functional water 90 and dissociation constant pKa of the hypochlorous acid.

Even when functional water 90 does not contain the pH adjuster as just described, it is possible to calculate the hypochlorous acid concentration using the pH of functional water 90. Note that pH meter 70 may measure the pH of functional water 90 containing the pH adjuster.

Outline

As described above, functional water concentration sensor 1 includes: light source 10 which emits ultraviolet light 11; container 20 capable of holding functional water 90 having a pH between 6 and 9, inclusive, and containing hypochlorous acid and hypochlorite dissociated from the hypochlorous acid, and including entry window 21 through which ultraviolet light 11 enters and exit window 22 through which ultraviolet light 11 that has entered container 20 through entry window 21 exits; light-receiving element 30 which includes light-receiving surface 30a facing exit window 22 and outputs an output signal according to an amount of light incident on light-receiving surface 30a; and signal processor 40. Signal processor 40 calculates the concentration of hypochlorite in functional water 90 on the basis of the output signal, calculates the percentages of the hypochlorous acid and the hypochlorite in functional water 90 on the basis of the pH of functional water 90 and dissociation constant pKa of the hypochlorous acid, and calculates the concentration of hypochlorous acid in functional water 90 on the basis of the calculated hypochlorite concentration and the calculated percentages.

Thus, functional water concentration sensor 1 can easily calculate the concentration of hypochlorous acid in functional water 90 on the basis of the pH of functional water 90.

Functional water concentration sensor 1a further includes temperature meter 60 which measures the temperature of functional water 90. Signal processor 40 corrects dissociation constant pKa of the hypochlorous acid on the basis of the measured temperature of functional water 90 and calculates the aforementioned percentages on the basis of the pH of functional water 90 and the corrected dissociation constant of the hypochlorous acid.

By correcting dissociation constant pKa of the hypochlorous acid on the basis of the temperature of functional water 90 in this manner, it is possible to increase the accuracy in calculating the concentration of hypochlorous acid in functional water 90.

Furthermore, for example, the pH of functional water 90 is within plus and minus one from dissociation constant pKa of the hypochlorous acid.

Thus, each of the percentage of the hypochlorite contained in functional water 90 and the percentage of the hypochlorous acid contained in functional water 90 does not become too low, making it possible to increase the accuracy in calculating the hypochlorous acid concentration.

Furthermore, for example, functional water 90 contains a pH adjuster.

This allows functional water concentration sensor 1 to calculate the hypochlorous acid concentration using the pH of functional water 90 that is maintained at a constant value by the pH adjuster.

Functional water concentration sensor 1a further includes temperature meter 60 which measures the temperature of functional water 90. Signal processor 40 corrects the pH of functional water 90 on the basis of the measured temperature of functional water 90 and calculates the aforementioned percentages on the basis of the corrected pH of functional water 90 and dissociation constant pKa of the hypochlorous acid.

By correcting the pH of functional water 90 on the basis of the temperature of functional water 90 in this manner, it is possible to increase the accuracy in calculating the concentration of hypochlorous acid in functional water 90.

Furthermore, for example, the absorbance of ultraviolet light 11 by the pH adjuster is less than the absorbance of ultraviolet light 11 by the hypochlorite.

Thus, upon calculation of the hypochlorite concentration, the effects of absorption of ultraviolet light 11 by the pH adjuster are small, making it possible to improve the accuracy in calculating the hypochlorite concentration.

Furthermore, for example, the pH adjuster has low reactivity with each of the hypochlorous acid and the hypochlorite.

This leads to reductions in variations in the hypochlorous acid concentration and variations in the hypochlorite concentration that result from the pH adjuster being contained, making it possible to improve the accuracy in calculating the hypochlorous acid concentration.

Furthermore, for example, the pH adjuster is a phosphate buffer.

The phosphate buffer hardly absorbs ultraviolet light 11 which the hypochlorite absorbs; thus, the effects of absorption of ultraviolet light 11 by the pH adjuster are small upon calculation of the hypochlorite concentration. This makes it possible to improve the accuracy in calculating the hypochlorite concentration.

Functional water concentration sensor 1b further includes pH meter 70 which measures the pH of functional water 90. Signal processor 40 calculates the aforementioned percentages on the basis of the measured pH of functional water 90 and dissociation constant pKa of the hypochlorous acid.

Thus, even when functional water 90 does not contain the pH adjuster, it is possible to calculate the hypochlorous acid concentration using the pH of functional water 90.

The method for calculating the concentration of hypochlorous acid in functional water 90 using functional water concentration sensor 1 includes: calculating the concentration of hypochlorite in functional water 90 on the basis of the output signal from light-receiving element 30 included in functional water concentration sensor 1; calculating the percentages of hypochlorous acid and hypochlorite in functional water 90 on the basis of the pH of functional water 90 and dissociation constant pKa of the hypochlorous acid; and calculating the concentration of hypochlorous acid in functional water 90 on the basis of the calculated hypochlorite concentration and the calculated percentages.

According to the calculation method just described, it is possible to easily calculate the concentration of hypochlorous acid in functional water 90 on the basis of the pH of functional water 90.

Other Embodiments

Although the exemplary embodiments have been hereinbefore described, the present invention is not limited to the above exemplary embodiments.

In the above exemplary embodiments, hypochlorous acid water has been given as an example of the functional water. However, the functional water concentration sensors according to the above exemplary embodiments may be used as sensors that measure the concentration of other types of functional water such as ozonated water. For example, the functional water concentration sensor may be a sensor to be used for functional water containing acid and anions dissociated from the acid. In this case, when the anions absorb visible light or infrared light, the functional water concentration sensor may include a light source that emits visible light or infrared light instead of ultraviolet light.

Furthermore, in the above exemplary embodiments, the light source, the container, the light diffuser, and the light-receiving element are arranged in this order on substantially the same straight line, but, for example, if a reflective member is disposed in the optical path, these structural elements can be arranged in a pattern different from substantially the same straight line.

Furthermore, although the light source and the light-receiving element are arranged outside the container in the above exemplary embodiments, this is not limiting. For example, the light source may be attached to the entry window. In other words, the light-emitting surface of the light source may be exposed in the container.

Forms obtained by various modifications to the exemplary embodiments that can be conceived by a person having ordinary skill in the art as well as forms realized by arbitrarily combining structural elements and functions in the respective exemplary embodiments which are within the scope of the essence of the present invention are included in the present invention.

The invention claimed is:

1. A functional water concentration sensor, comprising:
a light source which emits ultraviolet light;
a container including an entry window through which the ultraviolet light enters and an exit window through which the ultraviolet light that has entered the container through the entry window exits, the container for holding functional water having a pH between 6 and 9, inclusive, and containing hypochlorous acid and hypochlorite dissociated from the hypochlorous acid;
a light-receiving element which includes a light-receiving surface facing the exit window and outputs an output signal according to an amount of light incident on the light-receiving surface; and
a signal processor configured to calculate a concentration of the hypochlorite in the functional water based on the output signal, calculate percentages of the hypochlorous acid and the hypochlorite in the functional water based on the pH of the functional water and a dissociation constant of the hypochlorous acid, and calculate a concentration of the hypochlorous acid in the functional water based on the concentration of the hypochlorite calculated and the percentages calculated,
wherein:
the pH of the functional water is within plus and minus one from the dissociation constant of the hypochlorous acid,
the functional water contains a pH adjuster, and
the pH of the functional water is adjusted to a value between 6 and 9, inclusive, by the pH adjuster.

2. The functional water concentration sensor according to claim 1, further comprising:
a temperature meter which measures a temperature of the functional water, wherein
the signal processor corrects the dissociation constant of the hypochlorous acid based on the temperature of the functional water measured, and calculates the percentages based on the pH of the functional water and the dissociation constant of the hypochlorous acid corrected.

3. The functional water concentration sensor according to claim 1, further comprising:
a temperature meter which measures a temperature of the functional water, wherein
the signal processor corrects the pH of the functional water based on the temperature of the functional water measured, and calculates the percentages based on the pH of the functional water corrected and the dissociation constant of the hypochlorous acid.

4. The functional water concentration sensor according to claim 1, wherein
absorbance of the ultraviolet light by the pH adjuster is less than absorbance of the ultraviolet light by the hypochlorite.

5. The functional water concentration sensor according to claim 1, wherein
the pH adjuster has low reactivity with each of the hypochlorous acid and the hypochlorite.

6. The functional water concentration sensor according to claim 4, wherein
the pH adjuster is a phosphate buffer.

7. A method for calculating a concentration of hypochlorous acid in functional water using a functional water concentration sensor including:
a light source which emits ultraviolet light;
a container including an entry window through which the ultraviolet light enters and an exit window through which the ultraviolet light that has entered the container through the entry window exits; and
a light-receiving element which includes a light-receiving surface facing the exit window and outputs an output signal according to an amount of light incident on the light-receiving surface,
the method comprising:
storing the functional water in the container, the functional water containing the hypochlorous acid and hypochlorite dissociated from the hypochlorous acid, wherein a pH of the functional water is adjusted by a pH adjuster contained in the functional water to have a constant value between 6 and 9, inclusive, and the pH of the functional water is within plus and minus one from the dissociation constant of the hypochlorous acid;
calculating a concentration of the hypochlorite in the functional water based on the output signal;
calculating percentages of the hypochlorous acid and the hypochlorite in the functional water based on the pH of the functional water and a dissociation constant of the hypochlorous acid; and
calculating a concentration of the hypochlorous acid in the functional water based on the concentration of the hypochlorite calculated and the percentages calculated.

8. The method according to claim 7, further comprising:
correcting the dissociation constant of the hypochlorous acid based on a temperature of the functional water; and
calculating the percentages based on the pH of the functional water and the dissociation constant of the hypochlorous acid corrected.

9. The method according to claim 7, further comprising:
correcting the pH of the functional water based on a temperature of the functional water; and
calculating the percentages based on the pH of the functional water corrected and the dissociation constant of the hypochlorous acid.

10. The method according to claim 7, wherein
absorbance of the ultraviolet light by the pH adjuster is less than absorbance of the ultraviolet light by the hypochlorite.

11. The method according to claim 7, wherein
the pH adjuster has low reactivity with each of the hypochlorous acid and the hypochlorite.

12. The method according to claim 7, wherein
the pH adjuster is a phosphate buffer.

* * * * *